(12) United States Patent
De Franciscis et al.

(10) Patent No.: US 9,125,930 B2
(45) Date of Patent: Sep. 8, 2015

(54) EGFR APTAMER INHIBITOR FOR USE IN THERAPY AND DIAGNOSIS

(75) Inventors: Vittorio De Franciscis, Naples (IT); Laura Cerchia, Naples (IT)

(73) Assignee: CONSIGLIO NAZIONALE DELLE RICERCHE, Rome (IT)

( * ) Notice: Subject to any disclaimer, the term of this patent is extended or adjusted under 35 U.S.C. 154(b) by 78 days.

(21) Appl. No.: 13/876,111

(22) PCT Filed: Oct. 10, 2011

(86) PCT No.: PCT/EP2011/067629
§ 371 (c)(1),
(2), (4) Date: Mar. 26, 2013

(87) PCT Pub. No.: WO2012/049112
PCT Pub. Date: Apr. 19, 2012

(65) Prior Publication Data
US 2013/0177556 A1   Jul. 11, 2013

(30) Foreign Application Priority Data
Oct. 12, 2010   (IT) .............................. RM2010A0536

(51) Int. Cl.
| C07H 21/04 | (2006.01) |
| C12N 15/11 | (2006.01) |
| A61K 31/7088 | (2006.01) |
| C12N 15/115 | (2010.01) |
| A61K 39/395 | (2006.01) |
| A61K 45/00 | (2006.01) |

(52) U.S. Cl.
CPC ............ *A61K 31/7088* (2013.01); *A61K 39/395* (2013.01); *A61K 45/00* (2013.01); *C12N 15/115* (2013.01); *C12N 2310/16* (2013.01); *C12N 2310/322* (2013.01); *C12N 2310/344* (2013.01)

(58) Field of Classification Search
CPC ..................... C12N 2310/16; C12N 2310/322; C12N 2310/344
See application file for complete search history.

(56) References Cited

U.S. PATENT DOCUMENTS

2011/0166213 A1*   7/2011   De Franciscis et al. .... 514/44 R

FOREIGN PATENT DOCUMENTS

| EP | 2159286 A1 | 3/2010 |
| WO | 2005/040339 A2 | 5/2005 |
| WO | WO2010/023327 A2 * | 3/2010 |

OTHER PUBLICATIONS

Chen, C-H B., et al: "Inhibition of heregulin signaling by an aptamer that preferentially binds to the oligomeric form of human epidermal growth factor receptor-3", Proceedings of the National Academy of Sciences of the United States (PNAS), National Academy of Science, US, vol. 100, No. 16, Aug. 5, 2003, pp. 9226-9231, XP002303440, ISSN: 0027-8424, DOI: DOI:10.1073/PNAS.1332660100, p. 9226, col. 2-p. 9227, col. 1, paragraph 1, p. 9231, col. 2, paragraph 1.

Li, Na., et al: "Technical and Biological Issues Relevant to Cell Typing with Aptamers", Journal of Proteome Research, ACS, Washington, DC, US, vol. 8, No. 5, May 1, 2009, pp. 2438-2448, XP009137502, ISSN: 1535-3893, DOI: DOI:10.1021/PR801048Z [retrieved on Mar. 9, 2009], p. 2438, col. 2, p. 2439; table 1, p. 2446; col. 2, paragraph 2.

Bardelli, Alberto, et al: "Molecular mechanisms of resistance to cetuximab and panitumumab in colorectal cancer", Journal of Clinical Oncology, American Society of Clinical Oncology, US, vol. 28, No. 7, Mar. 1, 2010, pp. 1254-1261, XP008125621, ISSN: 0732-183X, DOI: 10.1200/JCO.2009.24.6116 [retrieved on Jan. 25, 2010], p. 1254, col. 2, paragraph 2-p. 1255, col. 1, paragraph 1 p. 1257, col. 1, paragraph 1.

* cited by examiner

*Primary Examiner* — Brian Whiteman
(74) *Attorney, Agent, or Firm* — Lucas & Mercanti, LLP

(57) ABSTRACT

The present invention concerns a nucleotide aptamer having the sequence 5' GCCUUAGUAACGUGCUUUGAUGUCGAUUCGACAGGAGGC3' (SEQ ID No. 1) for use in the treatment and/or prevention and/or diagnosis of an EGFR induced disorder and a pharmaceutical composition comprising the same. The invention also relates to a method for the diagnosis of a EGFR induced disorder in a patient from which a sample is obtained and relative diagnostic kit.

12 Claims, 15 Drawing Sheets

A

CL4 42-81 short :    GCCUUAGUAACGUGCUUUGAUGUCGAUUCGACAGGAGGC (SEQ ID NO.: 1)

B (SEQ ID NO.: 1)

A
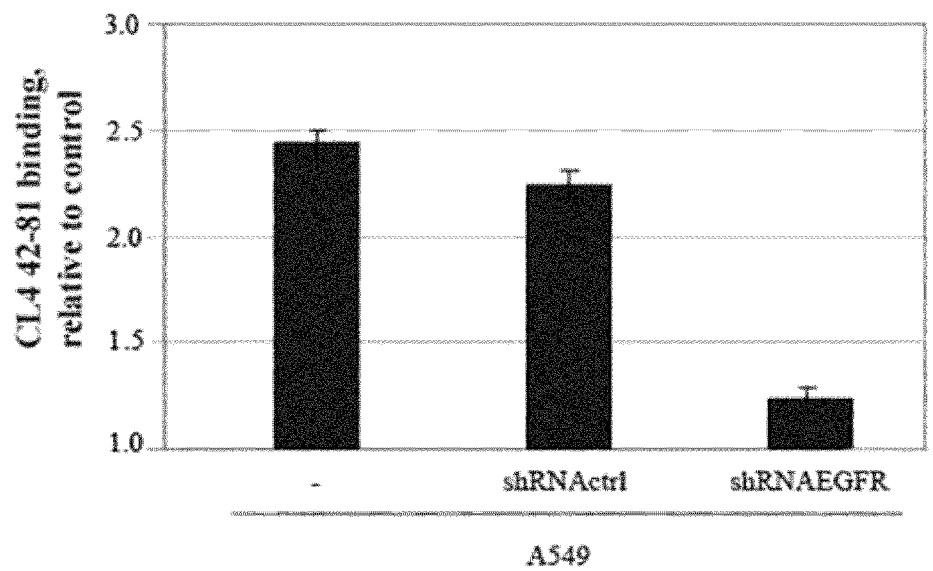
A1
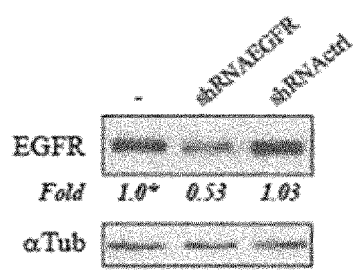
Figure 2(1/2)

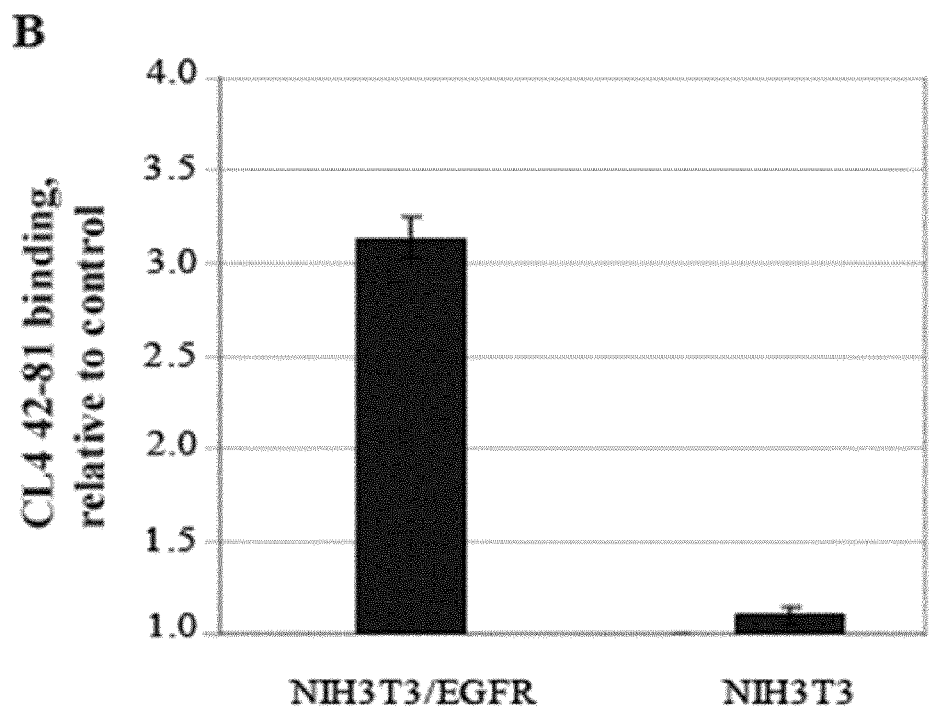
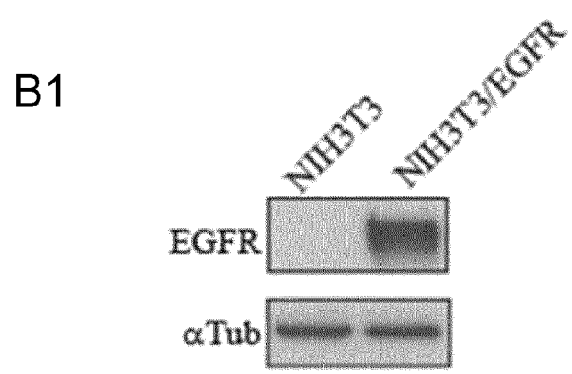
Figure 2(2/2)

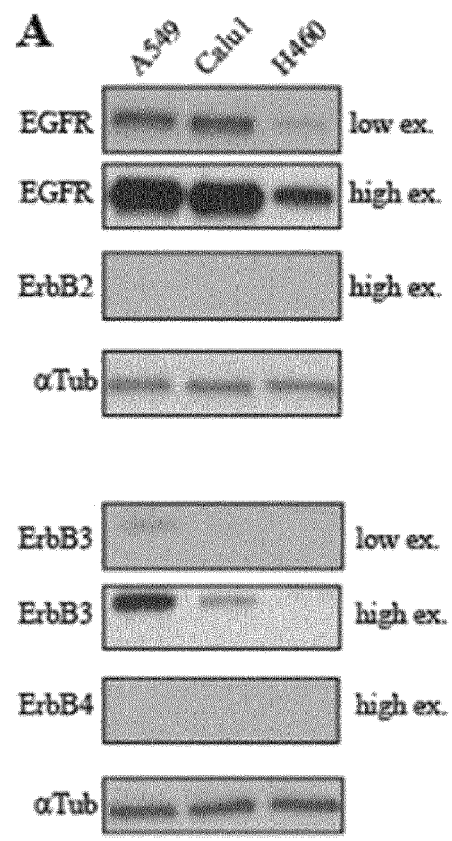
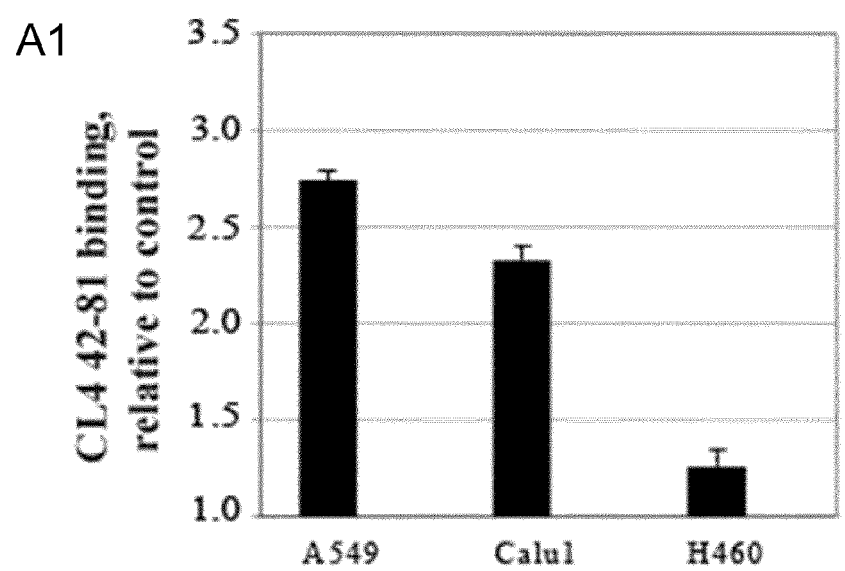
Figure 3 (1/2)

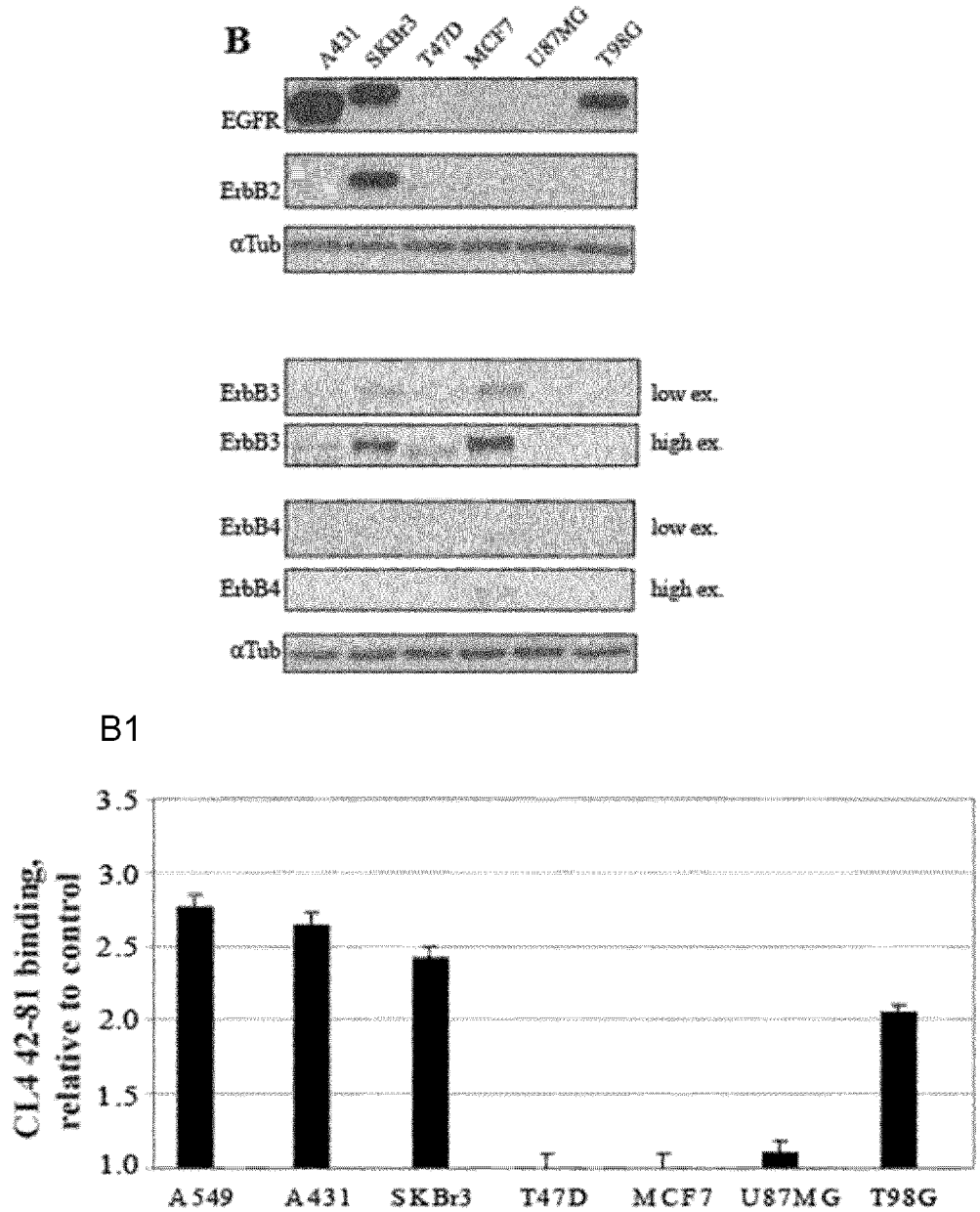
Figure 3 (2/2)

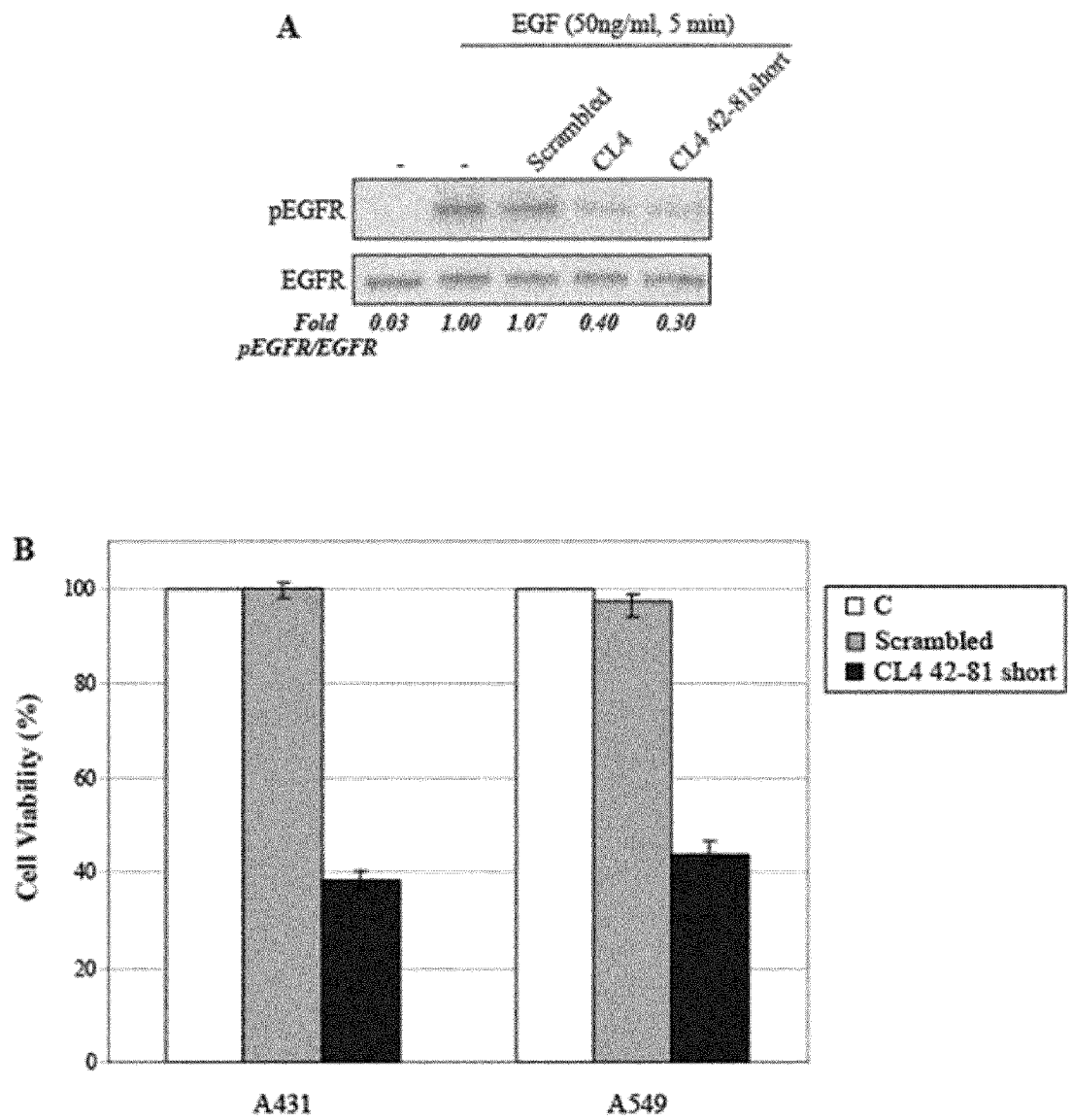
Figure 5 (1/2)

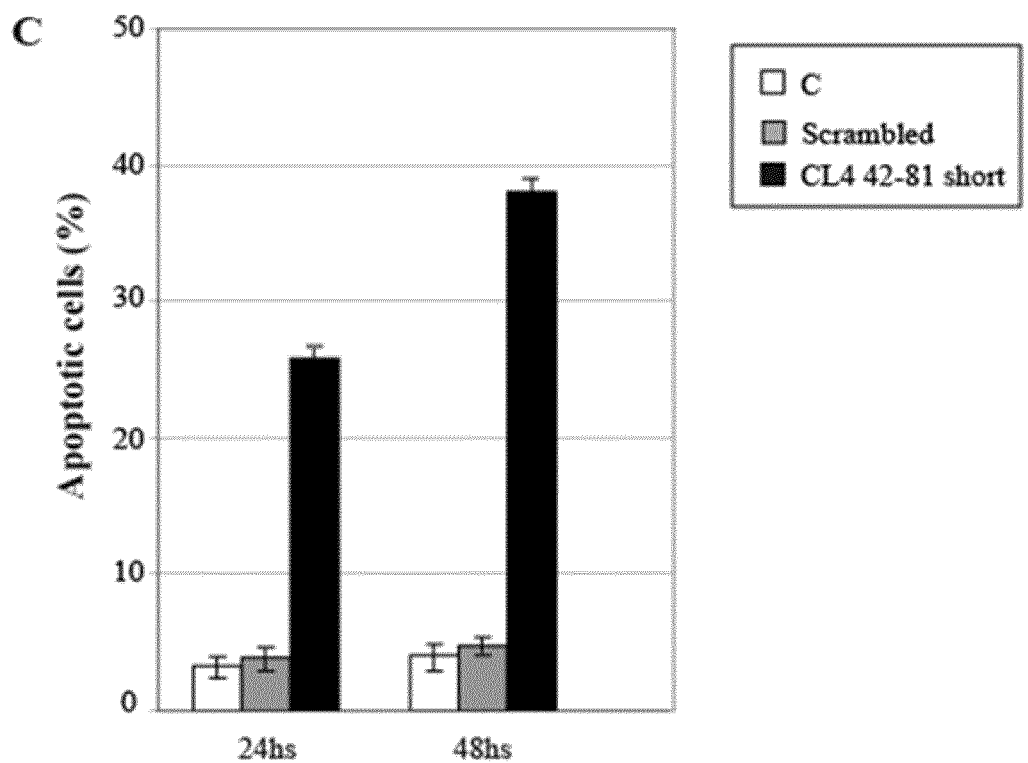
Figure 5 (2/2)

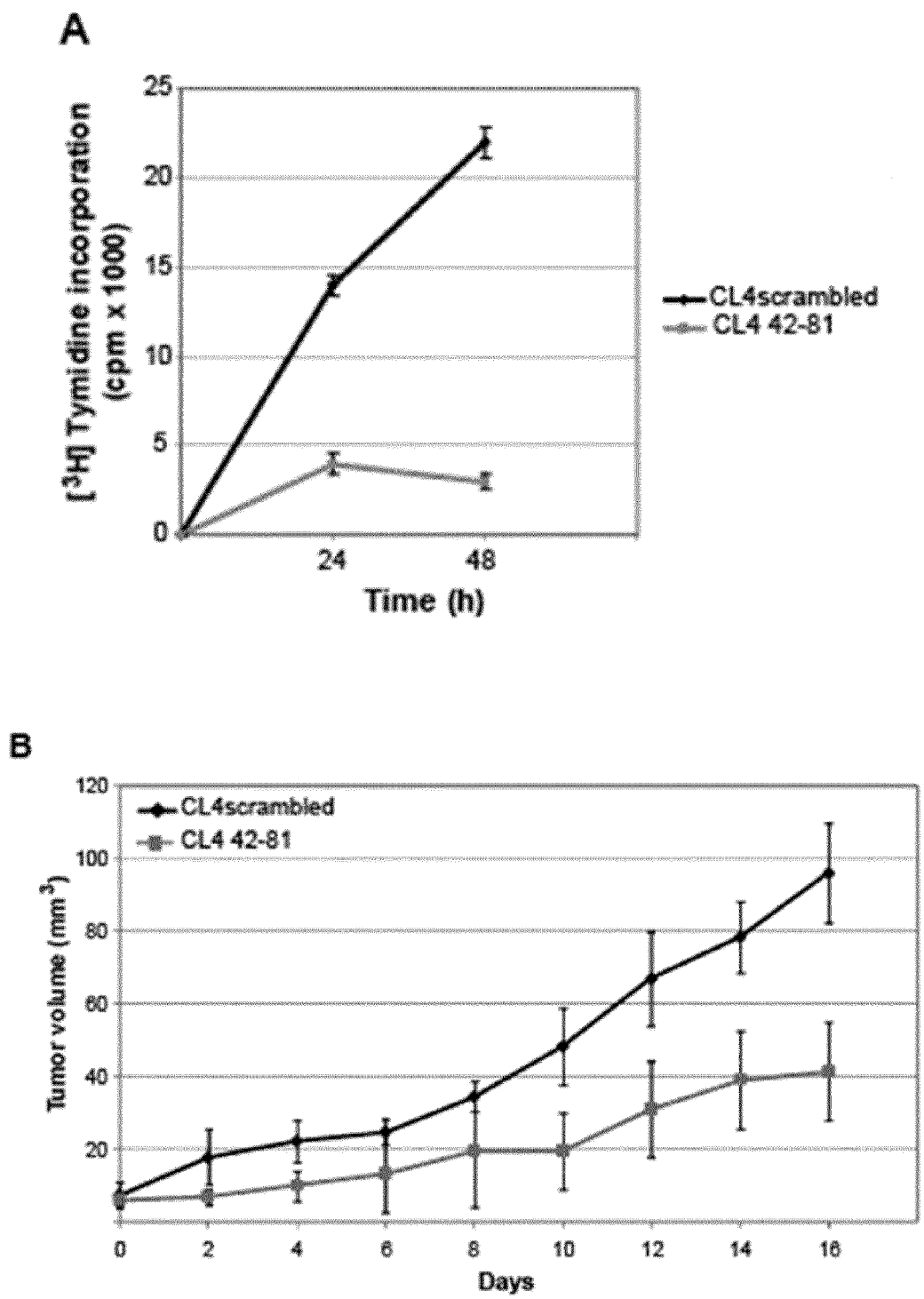
Figure 8 (1/2)

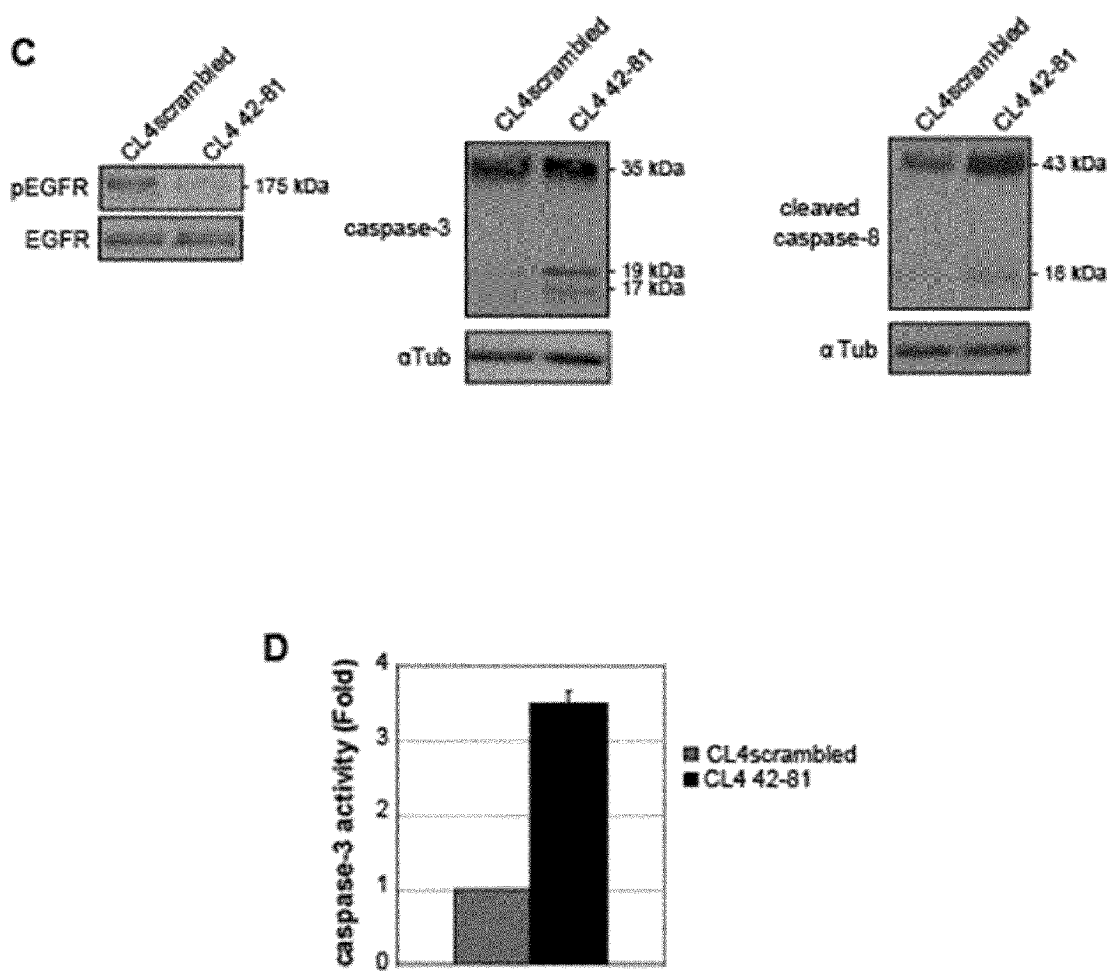
Figure 8 (2/2)

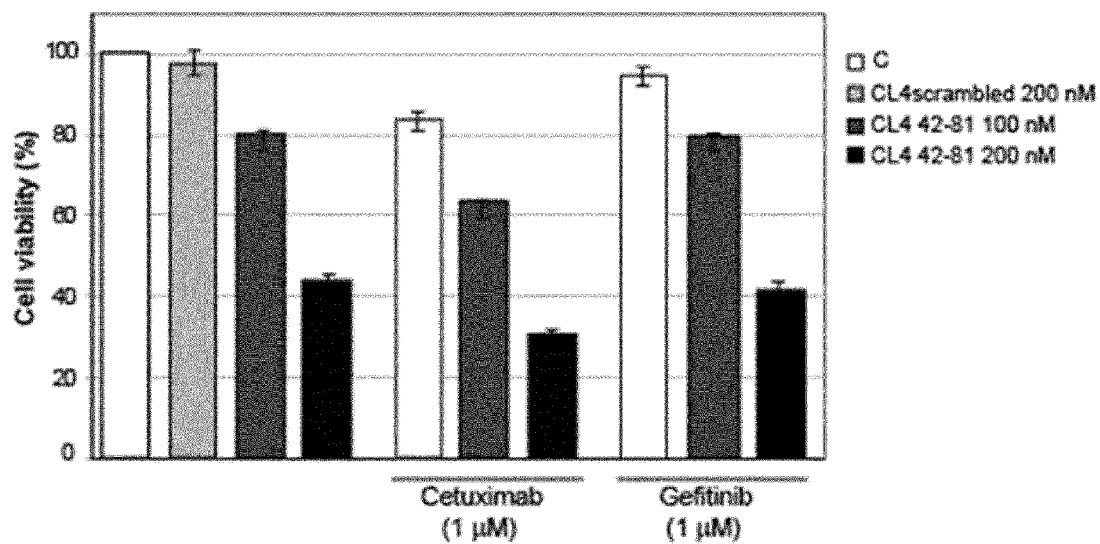
Figure 9 (1/3)

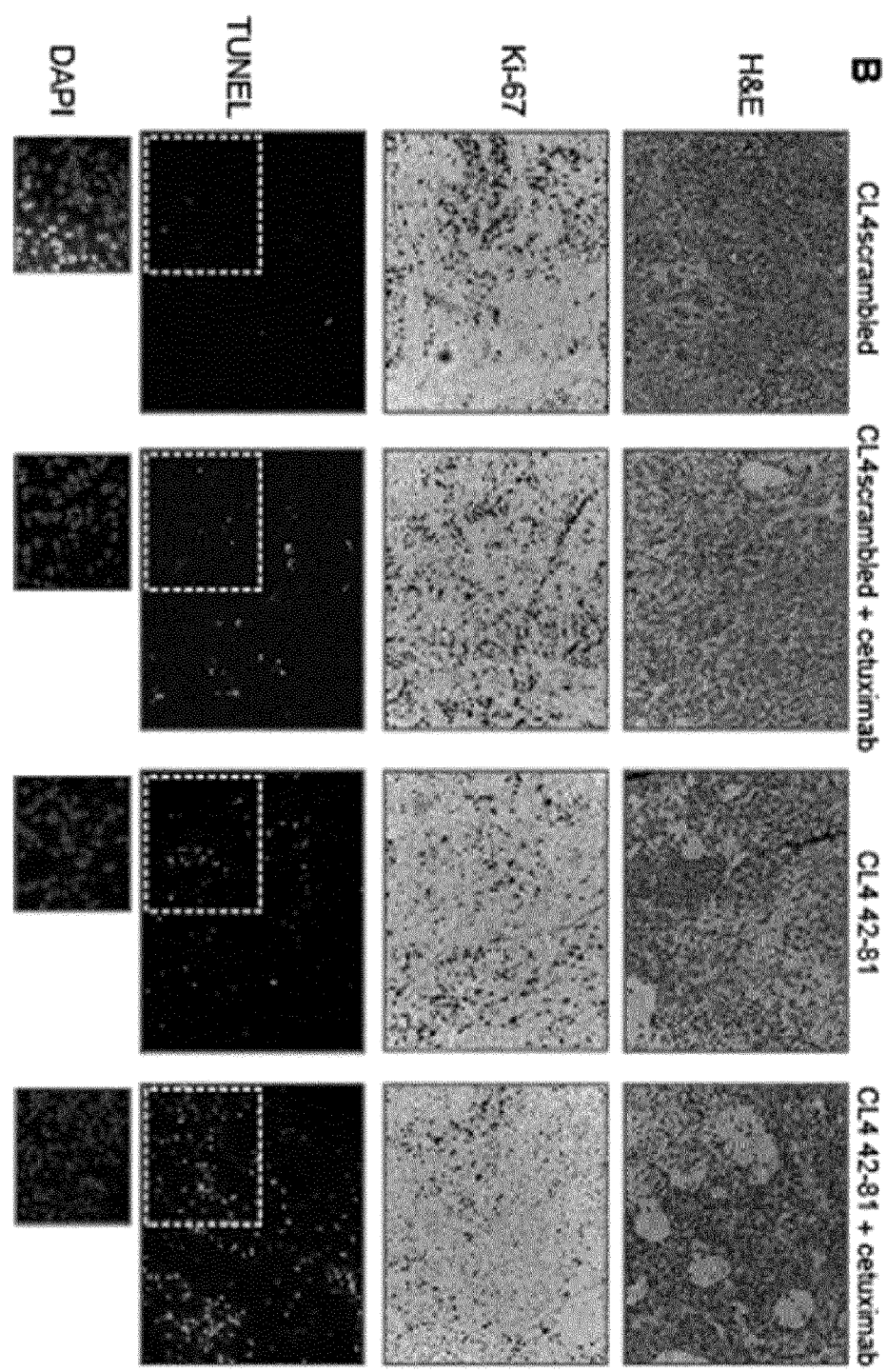
Figure 9 (2/3)

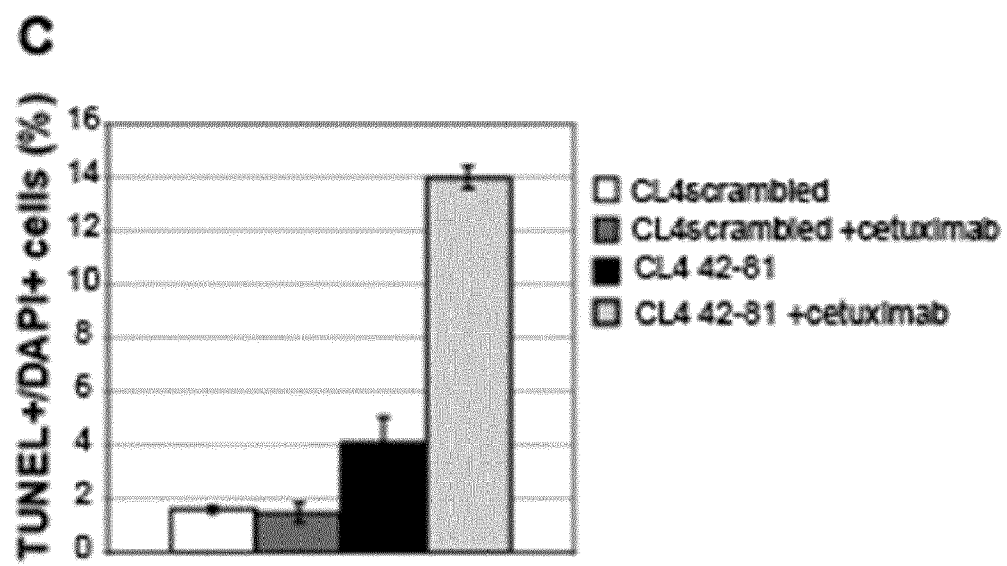
Figure 9 (3/3)

SEQUENCE LISTING

<160> NUMBER OF SEQ ID NOS: 4

<210> SEQ ID NO 1
<211> LENGTH: 39
<212> TYPE: RNA
<213> ORGANISM: Artificial Sequence
<220> FEATURE:
<223> OTHER INFORMATION: synthetic aptamer

<400> SEQUENCE: 1
gccuuaguaa cgugcuuuga ugucgauucg acaggaggc                          39

<210> SEQ ID NO 2

-continued

```
<211> LENGTH: 39
<212> TYPE: RNA
<213> ORGANISM: Artificial Sequence
<220> FEATURE:
<223> OTHER INFORMATION: synthetic control aptamer

<400> SEQUENCE: 2
uucguaccgg guagguuggc uugcacauag aacguguca                              39

<210> SEQ ID NO 3
<211> LENGTH: 97
<212> TYPE: DNA
<213> ORGANISM: Artificial Sequence
<220> FEATURE:
<223> OTHER INFORMATION: synthetic hairpin

<400> SEQUENCE: 3
tgctgttgac agtgagcgcg gtccttggga atttggaaat tagtgaagcc acagatgtaa       60
tttccaaatt cccaaggacc atgcctactg cctcgga                               97

<210> SEQ ID NO 4
<211> LENGTH: 92
<212> TYPE: RNA
<213> ORGANISM: Artificial Sequence
<220> FEATURE:
<223> OTHER INFORMATION: synthetic aptamer CL4

<400> SEQUENCE: 4
gggagacaag aauaaacgcu caacgacacg uugccagccg gagccuuagu aacgugcuuu       60
gaugucgauu cgacaggagg cucacaacag gc                                    92
```

EGFR APTAMER INHIBITOR FOR USE IN THERAPY AND DIAGNOSIS

CROSS-REFERENCE TO RELATED APPLICATIONS

This application is a 371 of PCT/EP2011/067629, filed Oct. 10, 2011, which claims the benefit of Italian Patent Application No. RM2010A000536, filed Oct. 12, 2010, the contents of each of which are incorporated herein by reference.

FIELD OF THE INVENTION

The invention relates to the identification of an aptamer and its target the EGFR. The aptamer is shown to be a potent EGFR receptor inhibitor therefore is particularly suitable for use in the treatment and/or the diagnosis of a tumour expressing EGFR a EGFR induced disorder.

BACKGROUND TO THE INVENTION

In cancer an increasing number of proteins involved in cell growth, including growth factors, receptors, intracellular mediators and transcription factors have been found to be altered through multiple mechanisms of activation. Dysregulation of human epidermal growth factor receptor (EGFR) family by over-expression or constitutive activation promotes tumor processes including angiogenesis and metastasis and is associated with poor prognosis in many human malignancies (Yarden Y, 2001; Mitsudomi T and Yatabe Y, 2010). The EGFR/ErbB family of receptor tyrosine kinases (RTK) comprises the four members: EGFR (also known as HER1 or ErbB1), ErbB2 (Neu, HER2), ErbB3 (HER3) and ErbB4 (HER4), which are type I transmembrane glycoproteins containing an extracellular ligand binding region, a single membrane-spanning region and an intracellular tyrosine-kinase-containing domain. Unlike the rest of the ErbB family, ErbB3 lacks tyrosine kinase activity and ErbB2 has no known ligand. EGF and transforming growth factor α bind directly only to EGFR, whereas neuregulins (also known as heregulins) are specific for ErbB3 and ErbB4 (Hynes N E and Lane H A, 2005). Ligand-induced activation of EGFR by dimerization mediates the activation of multiple downstream signaling pathways e.g the mitogen-activated protein kinase (MAPK), phosphatidylinositol 3-kinase (PI3K)/AKT, and signal transducers and activators of transcription 3 (STAT 3), which play pivotal roles in cellular events such as proliferation and survival (Schlessinger, 2004; Lurje and Lenz, 2009).

Two major classes of EGFR inhibitors are in clinical use: the anti-ErbB monoclonal antibodies, that bind to the extracellular domain of EGFR on the surface of tumour cells and small-molecule tyrosine-kinase inhibitors (TKI) that compete with ATP for binding to the tyrosine-kinase domain of the receptor (Li et al., 2005; Spicer J and Harper P, 2005; de La Motte Rouge et al., 2007; Cardó-Vilaa et al., 2010). The treatment of tumour cells with these agents affects many of the intracellular pathways that are essential for cancer development and progression. However, despite clinical success, the vast majority of patients receiving these treatments show primary or acquired resistance to the inhibitors (Kruser T J and Wheeler D L, 2010). Thus, new strategies to overcome TKI resistance are under active exploration and there is the urgent need to design new EGFR-targeting drugs for a more specific and selective tumour therapy.

An emerging wave of targeted therapeutic molecules against RTKs is composed of nucleic acid-based aptamers. They are short structured single-stranded RNA or DNA ligands that bind with high selectivity and sensitivity, due to their specific three-dimensional shapes, to their target molecules. Aptamers have a number of important advantages over proteins as therapeutic reagents (Cerchia et al., 2002; Cerchia and de Franciscis 2010). Indeed, they are entirely chemically synthesized by an in vitro evolution-based approach named SELEX (Systematic Evolution of Ligands by EXponential enrichment), thus avoiding the use of animal cells and assuring a rapid production process with high batch fidelity Furthermore, aptamers can be readily chemically modified by the addition of polyethylene glycol and other moieties to enhance their bioavailability and pharmacokinetics. Aptamers are non-immunogenic and, in addition, RNA made with pyrimidines modified at the 2'-position, which renders them resistant to extracellular nucleases, are even less immunogenic than natural RNA.

Li et al performed an in vitro selection against the purified extracellular domain of EGFR. The resulting RNA aptamer was then used to deliver gold nanoparticles to the intracellular compartment of cancer cells, offering proof-of-concept for further delivery strategies with this aptamer (Li et al., 2010). No functionality has been associated to the aptamer by Li et al. In the present invention a neutralizing RNA-aptamer specifically inhibiting the EGFR was identified.

BRIEF DESCRIPTION OF THE INVENTION

The present invention relates to a nucleic acid aptamer, named CL4 42-81, consisting of 39 nucleotides (nt) that binds with high affinity and specificity and inhibits the EGFR and to its use for diagnostic and therapeutic purposes, including drug delivery.

It is therefore an object of the invention a nucleotide aptamer having the sequence: 5'-GCCU-UAGUAACGUGCUUUGAUGUCGAUUCGA-CAGGAGGC-3' (SEQ ID NO: 1) for use in the treatment and/or prevention and/or diagnosis of an EGFR induced disorder. Preferably the nucleotide aptamer is nuclease-resistant. Still preferably the nucleotide aptamer has at least one or all of the pyrimidine residues that are modified to 2'-fluoropyrimidines. In the present invention, the pyrimidine residues may also be modified as 2'-O-alkyl nucleotides, or 3' end cap and locked nucleic acids or as LNA modifications to significantly enhance RNA stability.

Preferably the EGFR induced disorder is caused by, associated with and/or accompanied by EGFR hyperfunction.

Still preferably the EGFR induced disorder is selected among hyperproliferative disorders. In a preferred embodiment, the EGFR induced hyperproliferative disorder is selected from the group consisting of cancer or primary tumour metastasis.

Yet preferably the cancer or primary tumour metastasis is selected from the group of: gastrointestinal cancer, prostate cancer, ovarian cancer, breast cancer, head and neck cancer, lung cancer, non-small cell lung cancer, cancer of the nervous system, kidney cancer, retina cancer, skin cancer, liver cancer, pancreatic cancer, genital-urinary cancer and bladder cancer.

Still preferably, the EGFR induced disorder is resistant to a treatment of cetuximab and/or gefitinib.

It is a further object of the invention a pharmaceutical composition comprising the nucleotide aptamer as defined above for use in the treatment and/or prevention of an EGFR induced disorder.

Preferably the pharmaceutical composition further comprises another therapeutic agent. Still preferably, the further therapeutic agent is cetuximab.

It is a further object of the invention a method for the diagnosis of an EGFR induced disorder in a patient from which a sample is obtained comprising:

incubating the sample with the nucleotide aptamer as defined above;

measuring the binding of the nucleotide aptamer to the sample.

Preferably the sample is a blood, serum or saliva sample, a biopsy, urine or cerebrospinal fluid.

It is a further object of the invention a kit for the diagnosis of an EGFR induced disorder in a patient from which a sample is obtained comprising the nucleotide aptamer of the present invention.

BRIEF DESCRIPTION OF THE DRAWINGS

The invention will be now illustrated by means of non limiting examples referring to the following figures.

FIG. 2. Binding of CL4 42-81 aptamer following EGFR gene silencing/expression A) Binding of CL4 42-81 aptamer on NSCLC A549 cells transfected (or not) with a specific EGFR shRNA. A non-related shRNA (shRNActrl) that does not target EGFR was used as a control. A1) Cell lysates from A549 cells transfected with a specific EGFR shRNA or control shRNA were immunoblotted with anti-EGFR (EGFR) antibodies. Filters were stripped and reprobed with anti-αtubulin antibodies to confirm equal loading. Values below the blots indicate signal levels relative to control arbitrarily set to 1 (labeled with asterisk). Intensity of bands has been calculated using the NIH Image Program on at least two different expositions to assure the linearity of each acquisition. B) Binding of CL4 42-81 aptamer on NIH3T3 or NIH3T3 cells stably transfected with human EGFR (NIH/EGFR). B1) Cell lysates from NIH3T3 cells or NIH/EGFR cells were immunoblotted with anti-EGFR antibodies. To confirm equal loading, filters were reprobed with anti-αtubulin antibodies. In A and B) Binding was performed incubating [$^{32}$P]-labeled aptamer on the cells in the same condition at 100 nM. The results are expressed relative to the background binding detected with a scrambled aptamer used as a negative control.

FIG. 3. Binding of CL4 42-81 aptamer on different cancer cells. A and B) Cell lysates from the indicated cell lines were immunoblotted with anti-EGFR (EGFR), anti-ErbB2 (ErbB2), anti-ErbB3 (ErbB3), anti-ErbB4 (ErbB4) antibodies. Filters were stripped and reprobed with anti-αtubulin antibodies to confirm equal loading. When indicated two different exposition times (low exposition, low ex. and high exposition, high ex) were reported. A1 and B1) Binding of CL4 42-81 aptamer on the indicated cell lines was performed incubating [$^{32}$P]-labeled aptamer on the cells in the same condition at 100 nM. The results are expressed relative to the background binding detected with the scrambled aptamer used as negative control.

FIG. 5. CL4 42-81 aptamer inhibits EGFR Activity. A) Cells were serum starved, either left untreated or treated for 3 h with 200 nM of CL4, CL4 42-81 short or the scrambled aptamer and then stimulated with EGF alone or in the presence of the indicated aptamers. Cell lysates were immunoblotted with anti-(phospho)-EGFR (pEGFR), anti-EGFR (EGFR) as indicated. Filters were stripped and reprobed with anti-αtubulin (Tub) antibodies to confirm equal loading. Values below the blots indicate signal levels relative to EGF stimulated controls arbitrarily set to 1 (labeled with asterisk). Intensity of bands have been calculated using the NIH Image Program on at least two different expositions to assure the linearity of each acquisition. B) Effect on cell viability. NSCLC A549 and epidermoid carcinoma A431 cells were left untreated or treated for 24 hs with CL4 42-81 or the scrambled aptamer as a negative control at 200 nM final concentration. Cell viability was analyzed as reported in Materials and Methods by MTT assay. The results are expressed relative to untreated cells arbitrary set to 100% of viability and are representative of at least three different experiments. C) A549 cells were left untreated or treated with CL4 42-81 or the scrambled aptamer as a negative control for 24 hs or 48 hs. FACS analyses following PI incorporation was used to determine the percentage of apoptotic cells. In B and C) "C" indicates untreated cells.

FIG. 8. (A) A549 cells (2,000 cells/well in 24-well plates) were treated for 24 h or 48 h with CL4 42-81 or CL4 scrambled (200 nM-final concentration) and proliferation was determined by [$^3$H]-thymidine incorporation. Vertical bars indicate the standard deviation values. (B) Growth inhibition of tumors in a mouse xenograft model bearing EGFR-positive A549 cells upon CL4 42-81 treatment (57% at 16 days compared to CL4 scrambled control group, P<0.01 by Mann-Whitney test). Day 0 marks the first day of injection. Data are shown as means±s.e.m. (n=8 tumors). (C) Three tumors per group selected randomly were excised, lysed, and the pooled lysates were immunoblotted with anti-pEGFR, anti-EGFR, anti-caspase-3, anti-cleaved caspase-8 and anti-αtubulin antibodies, as indicated. Molecular weights of indicated proteins are reported. (D) Cell lysates as in (C) were analyzed by caspase-3 fluorimetric assays.

FIG. 9. (A) A549 cells (4,000 cells/well in 96-well plates) were left untreated or treated for 24 h with CL4 scrambled (200 nM-final concentration) or CL4 42-81 (100 and 200 nM-final concentration) alone or in combination with 1 μM cetuximab or 1 μM gefitinib. Cell viability was analyzed as reported in Methods and was expressed as percent of viable treated cells with respect to control untreated cells (indicated with "C"). Error bars depict means±s.d. (n=4). (B) Representative sections of tumors from the CL4 scrambled, CL4 scrambled plus cetuximab, CL4 42-81, and CL4 42-81 plus cetuximab groups (see "Materials and Methods" for details) stained with H&E, Ki-67 antibody and TUNEL, as indicated. DAPI counterstaining of the boxed regions is shown. Note reduction in cell density in the CL4 42-81-treated section stained with H&E. Magnification, 20× for H&E and Ki-67 and 40× for TUNEL and DAPI. (C) Percentage of TUNEL+/DAPI+ cells, values represent mean±s.d. for 10 randomly selected fields.

BRIEF DESCRIPTION OF THE SEQUENCE LISTING

Figure 1:
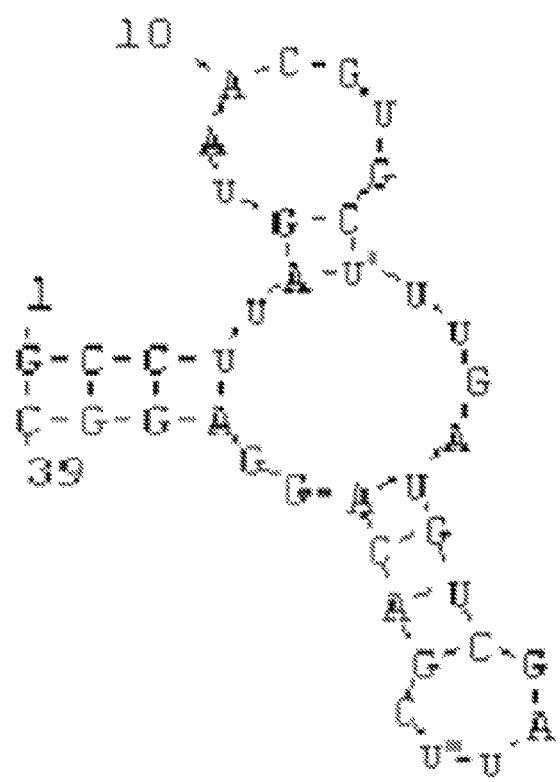
FIG. 1. CL4 42-81 aptamer. A) Nucleotide sequence of CL4 42-81 aptamer. All the pyrimidines of the sequence are 2'-fluoropyrimidine (2/F-Py), labelled in underlined. B) Secondary structure predicted for CL4 42-81 aptamer by using MFOLD software version 3.1 (available at http://www dot bioinfo dot rpi dot edu forward slash applications forward slash mfold/).

SEQ ID NO: 1 sets out sequence from the 5' of the aptamer, CL4 42-81 (see also FIG. 1), 5' GCCUUAGUAACGUGCUUUGAUGUCGAUUCGACAGGAGGC 3'.

SEQ ID NO: 2 sets out sequence from the 5' of the scrambled aptamer (CL4 scrambled) use as negative control in FIG. 3-9. 5' UUCGUACCGGGUAGGUUGGCUUGCACAUAGAACGUGUCA 3'.

SEQ ID NO: 3 sets out the sequence of a high performance short hairpin RNA (shRNA) specifically targeting EGFR (Oligo ID V2HS_201187) TGCTGTTGACAGTGAGCGCGGTCCTTGGGAATTTGGAAATT-AGTGAAGCCACA GATGTAATTTCCAAATTCCCAAG-GACCATGCCTACTGCCTCGGA.

SEQ ID NO: 4 sets out sequence from the 5' of the aptamer, CL4 (FIG. 5A) GGGAGACAAGAAUAAACGCUCAAC-GACACGUUGCCAGCCGGAGCCUUAGUA ACGUGCUUUGAUGUCGAUUCGACAGGAG-GCUCACAACAGGC.

DETAILED DESCRIPTION OF THE INVENTION

Materials and Methods
CL4 42-81 Aptamer
CL4 42-81 aptamer is a 2'-fluoropyrimidine (2'F-Py), nuclease-resistant RNA aptamer consisting of 39 nt:

(SEQ ID No. 1)
5' GCCUUAGUAACGUGCUUUGAUGUCGAUUCGACAGGAGGC 3'.

2'-fluoro (amino) pyrimidine modifications, 2'-O-alkyl nucleotides, 3' end cap and locked nucleic acids, LNA modifications, are the modification that significantly enhance RNA stability and may be used in the present invention.

CL4 42-81 aptamer and a scrambled sequence used as a negative control were purchased from Sigma (Sigma, St. Louis, Mo.).

Cells and shRNA Transfection
Human NSCLC A549, epidermoid carcinoma A431, glioma U87MG and T98G, breast SKBr3, MCF7 and T47D and mouse fibroblast NIH3T3 (all from American Type Culture Collection, Manassas, Va.) cells were grown in Dulbecco's modified Eagle medium (DMEM) supplemented with 10% fetal bovine serum (FBS) and 2 mM L-glutamine (Invitrogen, Carlsbad, Calif.). NIH3T3 cells stably transfected with human EGFR (NIH/EGFR) were grown in DMEM with 10% FBS and 2 mM L-glutamine supplemented with 50 µg/ml Gentamycin.

shRNA Transfection
EGFR gene silencing in NSCLC A549 cells was established by transfection of high performance short hairpin RNA (shRNA) specifically targeting EGFR (from Expression Arrest™ Human shRNA Collection, Open Biosystems, Huntsville, Ala.). Cells ($3.5 \times 10^5$ cells per 6 cm plate) were grown and overlaid with the transfection mixtures containing the shRNA (6 µg) against EGFR (referred as shRNAEGFR) and Lipofectamine 2000 (Invitrogen, Carlsbad, Calif.) in Opti-MEM I reduced serum medium (Invitrogen). After 5 hours incubation, complete culture medium was added to the cells and incubation was prolonged up to 72 hs. Controls were performed using a non-related shRNA (shRNActrl) that do not lead to the specific degradation of EGFR mRNA. For binding assays transfected cells were plated in 24 well plates after 24 hs from transfection.

Binding Assays
Binding experiments were performed with 5'-[$^{32}$P]-labeled RNA. For labeling 2'-F-Py RNAs were 5'-end dephosphorylated using bacterial alkaline phosphatase (Invitrogen, Carlsbad, Calif.) before [$^{32}$P]-5'-end-labeled using T4 kinase (Invitrogen) and γ-[$^{32}$P]-ATP ($6 \times 10^3$ Ci/mmol, GE Healthcare Bio-Sciences, Uppsala, Sweden) according to the supplier's instructions.

For binding experiments on cells, $3.5 \times 10^4$ cells were plated in 24-well plates in triplicate and were incubated with CL4 42-81 aptamer the scrambled sequence used as a negative control at 100 nM concentration in 200 µl of DMEM serum free for 20 min at RT in the presence of 100 µg/ml polyinosine as a nonspecific competitor (Sigma, St. Louis, Mo.). After five washings with 500 µl DMEM, bound sequences were recovered in 300 µl of SDS 1%, and the amount of radioactivity recovered was counted.

The aptamers ability to bind EGFR or ErbB3 soluble extracellular domain (EC-EGFR and EC-ErbB3) was investigated by filter binding by plotting the fraction of RNA bound to the nitrocellulose filter as a function of protein concentration, using the following equation:

$$RNA\ bound = \frac{B\max[\text{Protein}]}{Kd + [\text{Protein}]}$$

where Bmax is the extrapolated maximal amount of RNA: protein complex that will be bound. 1 nM of radiolabelled aptamers (CL4 42-81 aptamer or the scrambled sequence) were incubated with 1, 3.2, 10, 32, 100, 320 and 1000 nM of EC-EGFR and EC-ErbB3 (all from R&D Systems, Minneapolis, Minn.) for 15 min at 37° in phosphate-buffered saline (PBS) supplemented with 0.01% bovine serum albumin.

In order to test the binding for dimeric and monomeric proteins, 1 nM of radiolabelled aptamers (CL4 42-81 or scrambled) were incubated with 20 nM of EC-EGFR and EC-ErbB3 without or with 5 mM DTT.

After incubation, the aptamer-protein mix was passed through nitrocellulose membrane filter (Millipore Co., Bedford, Mass.) and filters were counted. In all binding assays the background values obtained with the scrambled RNA were subtracted from the values obtained with the CL4 42-81 aptamer.

Immunoblot Analyses
To assess the effects of aptamers on EGFR activity, A549 cells ($1.5 \times 10^5$ cells per 3.5-cm plate) were serum-starved over night, pretreated with 200 nM CL4 42-81 aptamer or the scrambled aptamer used as a negative control for 3 h and then stimulated for 30 min with 50 ng/ml EGF (R&D Systems, Minneapolis, Minn.) either alone or in presence of each aptamer. The aptamers were subjected to a short denaturation-renaturation step (85° C. for 5 min, snap-cooled on ice for 2 min, and allowed to warm up to 37° C.) before each treatment. To prepare cell extracts, cells were washed twice in ice-cold PBS, and lysed in buffer A (50 mM Tris-HCl pH 8.0 buffer containing 150 mM NaCl, 1% Nonidet P-40, 2 mg/ml aprotinin, 1 mg/ml pepstatin, 2 mg/ml leupeptin, 1 mM Na$_3$VO$_4$). Protein concentration was determined by the Bradford assay using bovine serum albumin as the standard. The cell lysates were subjected to SDS-PAGE. Gels were electroblotted into polyvinylidene difluoride membranes (Millipore Co., Bedford, Mass.), and filters were probed with the indicated primary antibodies: anti-EGFR and anti-phospho-EGFR (Tyr1062), anti-phospho-44/42 MAP kinase (E10) (also indicated as p-Erk), anti-phospho-Akt, anti-Akt and anti-phospho-STAT3 (Tyr705), anti-ErbB2 (all from Cell Signaling, Beverly, Mass., United States); anti-Erk1, anti-EGFR, anti-ErbB3, anti-ErbB4 (C-16) (Santa Cruz Biotechnology, California, United States); anti-α-αtubulin (DM 1A) (Sigma, St. Louis, Mo.).

Proteins were visualized with peroxidase-conjugated secondary antibodies using the enhanced chemiluminescence system (GE Healthcare Bio-Sciences, Uppsala, Sweden). Where indicated, filters were stripped in 62.5 mM Tris-HCl pH 6.8 with 100 mM 2-mercaptoethanol and 2% SDS for 30 min at 54° C., and reprobed.

Cell Viability Assay

Cell viability was assessed with CellTiter 96® AQueous One Solution Cell Proliferation Assay (Promega, Madison, Wis.) according to according to the supplier's instructions. Cells ($4\times10^3$ cells/well) were plated in 96-well plates in triplicate. and were treated for 24 hs with heat denatured CL4 42-81 or the scrambled aptamer at 3 µM concentration. RNA concentrations were determined to ensure the continuous presence of a concentration of at least 200 nM, which takes into account the 6 hs-half life of the aptamer in 10% serum. The optical density (OD) was measured using a Multilabel Counter (Bio-Rad) at a wavelength of 490 nm and cell viability was calculated by the following formula:

Cell viability (%)=(OD treated cells/OD control cells)×100%.

FACS Analysis

For apoptosis assay, DNA content analysis was performed by staining with propidium iodide (PI) and analyzing cells by flow cytometry (FACS).

A549 cells were plated in 96-well plates ($5.0\times10^3$ cells/each well) and treated with CL4 42-81 or the scrambled aptamer at 3 µM concentration for 24 hs and 48 hs renewing treatment each 24 hs. Cells were incubated with 2 µg/ml propidium iodide (PI, Sigma, St. Louis, Mo.) for 30 min at 4° C. and recovered. The relative proportion of cells with DNA content indicative of apoptosis (ipoploid) was determined by FACS.

Caspase Activity Assay

A549 cells were treated with 200 nM CL4 42-81 or the scrambled aptamer for 6 hs. To determine caspase activity cell lysates (50 µg) were incubated at 37° C. for 1 h with 50 µM of a specific fluorometric substrate (Ac-DEVD-AFC for caspase-3, Ac-IETD-AFC for caspase-8, both from Alexis Bichemicals, San Diego, Calif.). Cleavage of the fluorometric substrate were determined using a Fluorometer, with excitation at 400 nm and emission at 505 nm wavelengths.

[$^3$]-Thymidine Incorporation Assay

A549 cells were treated for 24 h or 48 h with CL4 42-81 or CL4 scrambled. During the final 6 h, cells were pulsed with 1 µCi/ml [$^3$H]-thymidine (45 Ci/mmol) (Amersham-Pharmacia Biosciences) added in complete growth medium and incubated at 37° C. At the end of each pulse, cells were harvested and [$^3$H]-thymidine incorporation was analyzed by a Beckman LS 1701 Liquid Scintillation Counter.

In Vivo Experiments

Athymic nude mice (nu/nu) were maintained in a sterile environment according to guidelines for Animal Care. Mice were inoculated with either $3\times10^6$ (in 100 µl) in vitro propagated A431 cells subcutaneously injected into each flank. Approximately 24 non-necrotic tumors for each tumor type, of about 1 cm in diameter, were randomly divided into three groups of eight mice per treatment group as follows: group 1, no treatment; group 2, treated with scrambled RNA as a negative control (200 pmols/injection); group 3, treated with CL4 42-81 (200 pmols/injection). Compounds were injected intra-tumorally in 100-1 µl volumes three times a week for two weeks. Day 0 marks the first day of injection. The aptamers may also be administered systemically, in particular when optimized by addition of polyethylene glycol (PEG).

The volume injections are small enough to preclude the compounds being forced inside the cells due to a nonspecific high-pressure injection. Tumors were measured every 3 days with calipers in three dimensions. The following formula was used to calculate tumor volume: $V_T=(W\times L\times H)\times0.5236$ (W, the shortest dimension; L, the longest dimension; H, the intermediate dimension). The growth curves are plotted as the means tumor volume±s.e.m. Statistical analysis of tumor size data was conducted using a one-way ANOVA. A P-value of 0.05 or less was considered to indicate a significant difference. Statistical analysis of tumor size data was conducted using a one-way ANOVA. A P-value of 0.05 or less was considered to indicate a significant difference.

Combined Treatment of CL4 42-81 and Cetuximab In Vivo in A549-Mouse Xenografts

Athymic CD-1 nude mice (nu/nu) were housed in a highly controlled microbiological environment, thus to guarantee specific pathogen free conditions. Mice were injected subcutaneously with $3\times10^6$ (in 100 µl) in vitro propagated A549. Sixteen non-necrotic tumors of about 0.5 cm in diameter were randomly divided into two groups of eight mice as follows: group 1, CL4 scrambled-treated; group 2, CL4 42-81-treated. Aptamers (200 pmols/injection) were injected intra-tumorally in 100-1 µl volumes three times a week for 16 days. Tumors were measured every 2 days. For combined treatment of CL4 42-81 and cetuximab, 24 non-necrotic tumors of about 0.5 cm in diameter were randomly divided into four groups of six mice as follows: group 1, CL4 scrambled (200 pmols/intratumor injection three times a week for 21 days); group 2, CL4 scrambled plus cetuximab (200 pmols/intratumor injection three times a week for 21 days, plus 25 µg cetuximab/intraperitoneal injection in 100-µl volumes once a week for the last 14 days); group 3, CL4 42-81 (200 pmols/intratumor injection three times a week for 21 days); group 4, CL4 42-81 plus cetuximab (200 pmols/intratumor injection three times a week for 21 days, plus 25 µg cetuximab/intraperitoneal injection in 100-µl volumes once a week for the last 14 days).

Histology and Immuno-Histochemistry

Tumors were embedded in paraffin and sectioned at 6 p.m. To inhibit the endogenous peroxidases, the sections were treated with 0.5% $H_2O_2$ in absolute methanol for 15 min at RT. For histological examinations, serial paraffin sections were stained with Harris hematoxylin and aqueous eosin (H&E, BDH Laboratory Supplies).

Cell proliferation was assessed by Ki-67 immunohistochemistry. The anti-human Ki-67 antibody (Epitomics) was 1:500 diluted and immunostaining was done using the immunoperoxidase system of the "Vectastain ABC kit" (Vector) and the "DAB substrate kit for peroxidise" (Vector), according with the manufacturer's protocol.

TUNEL Assay

Apoptotic cell death in paraffin tumor tissue sections was detected using TUNEL staining. Sections were permeabilized with 0.1% Triton X-100, 0.1% sodium citrate solution and apoptosis was detected with in situ Cell Death fluorescein kit (Roche) according to manufacturer's procedure. All staining were finally counterstained with DAPI before mounting.

Microscopy and imaging were performed in a Zeiss Axion-Plan II epifluorescence (FluoArc) Microscope. The images were processed using Axion Vision software and edited by Image J software.

Results

Identification of a RNA-Aptamer Specifically Interacting with the Extracellular Domain of the EGFR CL4 42-81 aptamer is a 2'-fluoropyrimidine (2'F-Py), nuclease-resistant RNA aptamer consisting of 39 nucleotides (nt) (FIG. 1). It was obtained by reducing the length of an aptamer (named CL4) that the authors have previously generated by a differential cell-SELEX approach on chemoresistant non small cell lung carcinoma (NSCLC) A549 cells. The adopted selection strategy was roughly the same that allowed the authors' to select RNA-aptamers as high specific and affinity ligands for highly tumorigenic glioma cell lines (Cerchia et al, 2009 PLoS One; 4(11):e7971, International Patent Application WO 2010/023327).

The CL4 42-81 aptamer was obtained on the basis of the predicted secondary structures and the presence of potential binding sites in the entire CL4 aptamer sequence (92 nt). The authors found that by removing 42 nucleotides from 5' terminus and 11 nucleotides from the 3' terminus of the long sequence preserved a secondary structure of 39 nucleotides in length (see FIG. 1). This minimal variant (herein named CL4 42-81) is sufficient to bind to A549 target cells displaying a Kd of 38 nM and discriminate them from H460 cells (see FIG. 3). The Kd value for CL4 sequence is 46 nM.

The authors have identified the EGFR receptor as the target of CL4 42-81 aptamer. The ability of CL4 42-81 aptamer to bind to A549 cells is significantly reduced upon decreased EGFR expression by means of a specific shRNA (FIG. 2A). Conversely, CL4 42-81 binds NIH3T3 cells stably transfected with human EGFR (NIH/EGFR) whereas it does not binding on parental NIH3T3 cells (FIG. 2B).

Accordingly, binding analyses with the CL4 42-81 aptamer on NSCLC and unrelated cancer cell lines show that the binding of the aptamer correlates with an high EGFR expression in the analysed cells (FIG. 3).

Indeed, among the NSCLC tested, CL4 42-81 binds EGFR-positive A549 and Calu1 cells, whereas it does not bind to H460 cells that express low level of EGFR receptor (FIG. 3A1). Furthermore, CL4 42-81 does not bind human glioma U87MG, breast MCF7 and T47D that are all characterised by no or very low expression of EGFR (FIG. 3B, 3B1), while it binds glioma T98G, breast SKBR3 and epidermoid carcinoma A431 cells expressing high level of EGFR (FIG. 3B, 3B1).

In agreement with previous reports (Amann et al., 2005), ErbB2 and ErbB4 expression was undetectable in all these cell lines, whereas ErbB3 was detected at a very low level in A549 and Calu1 cells (FIG. 3A). No correlation was found between CL4 42-81 aptamer binding and the expression level of ErbB2, ErbB3 or ErbB4 in the analysed cell lines (see FIG. 3A).

Figure 4:
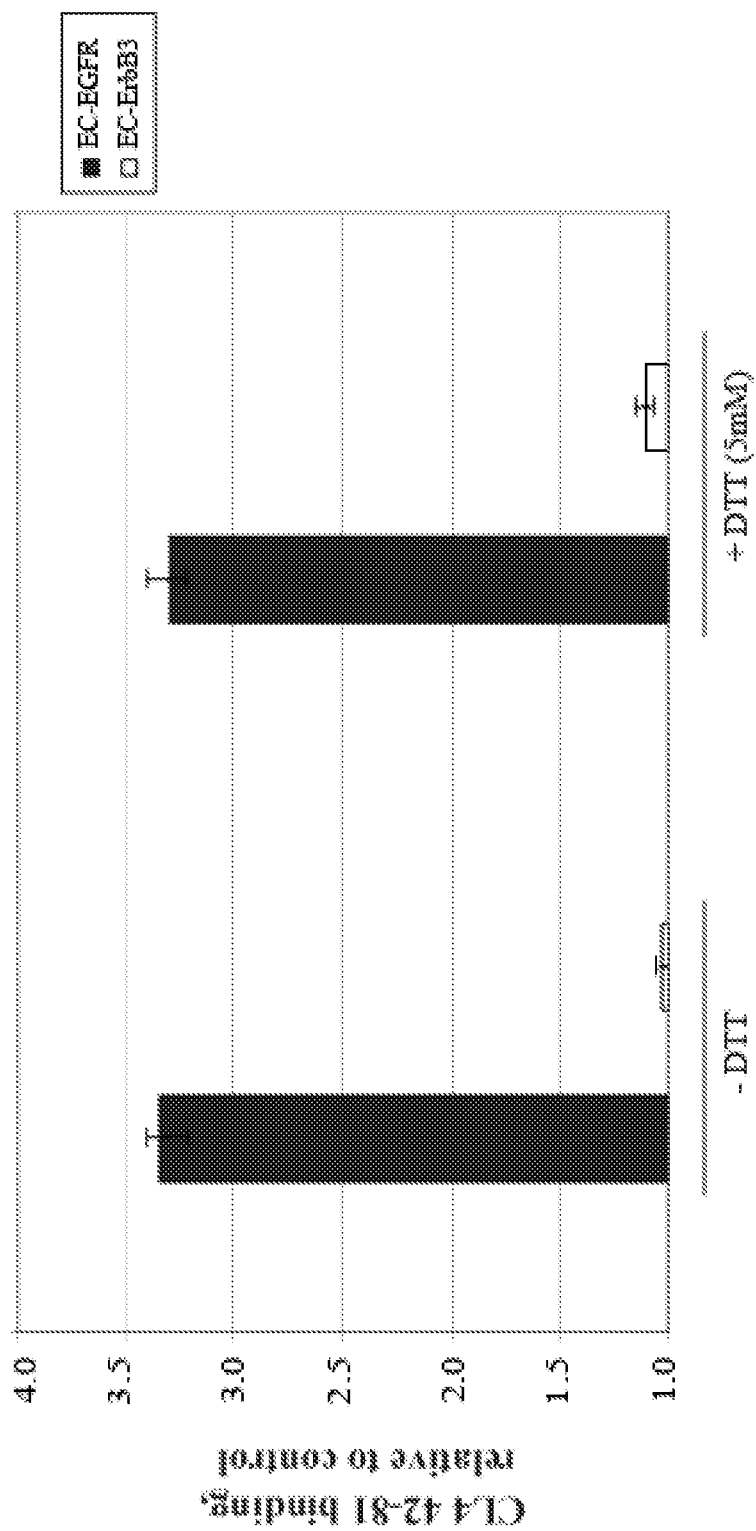
FIG. 4. Binding on purified EGFR receptor. CL4 42-81 aptamer was incubated with the soluble extracellular domain of EGFR (EC-EGFR) or ErbB3 (EC-EGFR) with or without DTT treatment as reported in Materials and Methods. The results are expressed relative to the background binding detected with the scrambled sequence.

The CL4 42-81 aptamer recognizes specifically the EGFR expressed on the surface of cancer cells as well as the purified soluble extracellular domain of the receptor (FIG. 4). Indeed a filter binding analysis performed with the soluble extracellular domain of human EGFR and ErbB3 as targets (indicated as EC-EGFR and EC-ErbB3, respectively) confirmed a strong affinity of CL4 42-81 for EC-EGFR (Kd of 10 nM). Regarding the binding to the extracellular domain of ErbB3 (EC-ErbB3 protein), under the protein concentration used, no Kd value could be calculated indicating that the aptamer does not bind to EC-ErbB3 or binds to the protein but with an affinity of a magnitude at least $10^3$ lower. The purified EC domain used for binding assays is a disulfide-linked homodimer thus can be rendered into a monomer by the addition of 5 mM DTT. As shown in FIG. 4, CL4 42-81 aptamer has a similar affinity for both the EGFR dimer and monomer in vitro.

The CL4 42-81 Aptamer Inhibits the EGFR-Mediated Signal Pathways

As a next step, the authors wondered whether CL4 42-81 could affect EGFR activation following EGF stimulation of A549 target cells. As shown in FIG. 5A, CL4 42-81 treatment drastically reduces the EGF-dependent phosphorylation of EGFR reaching 60% inhibition following 5 min of EGFR stimulation. No effect was observed in the presence of the scrambled aptamer used as negative control.

As a consequence of the EGFR inhibition, CL4 42-81 treatment decreases the EGF-induced phosphorylation of the downstream effectors anti-apoptotic signal transducer and activator of transcription protein 3 (STAT 3) and ERK (not shown).

The identification of an aptamer that specifically binds and inhibits EGFR, hampering the anti-apoptotic STAT3 pathway, raises the obvious question of whether this aptamer may interfere with survival of EGFR-positive target cells. As shown in FIG. 5B, a 24-hs-treatment of A549 and A431 cells with CL4 42-81 aptamer strongly inhibited cell viability to about 60% by comparison with cells untreated or treated with the scrambled aptamer. In order to dissect the molecular mechanism of CL4 42-81 induced cell viability reduction, the authors analyzed apoptosis in A549 cells following aptamer treatment. Cells were treated with CL4 42-81 aptamer or the scrambled aptamer (200 nM-final concentration) and the apoptotic sub-G1 peak was analysed. Remarkably, the authors found that the percentage of apoptotic cells was about 30% after 24 hs of CL4 42-81 treatment outgoing to 40% after 48 hs (FIG. 5C). No effect was observed in the presence of scrambled aptamer negative control.

Figure 6:
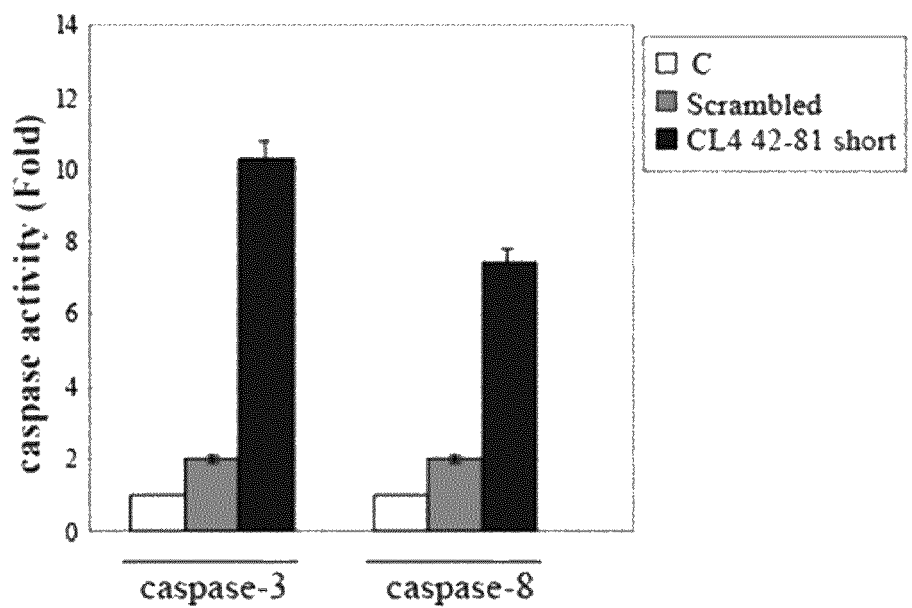
FIG. 6. To determined caspase-3 activation, A549 cells were left untreated or treated with CL4 42-81 or the scrambled aptamer as a negative control for 6 hs. Caspase-3 or caspase-8 activity was evaluated by measuring hydrolysis of their specific fluorogenic substrate as reported in Materials and Methods. The activation was expressed relatively to untreated cells, (indicated as "C") arbitrarily set to 1.

Further, CL4 42-81 is able to strongly induce activation of caspase-3 and caspase-8 (FIG. 6).

CL4 42-81 Suppresses Tumor Growth In Vivo

The authors wondered whether CL4 42-81 aptamer could interfere with tumor growth in vivo. Nude mice were inoculated with the epidermoid carcinoma cell line A431 which expresses high levels of EGFR and tumors were allowed to grow until they reached about 1 cm in diameter in the longest dimension.

Figure 7:
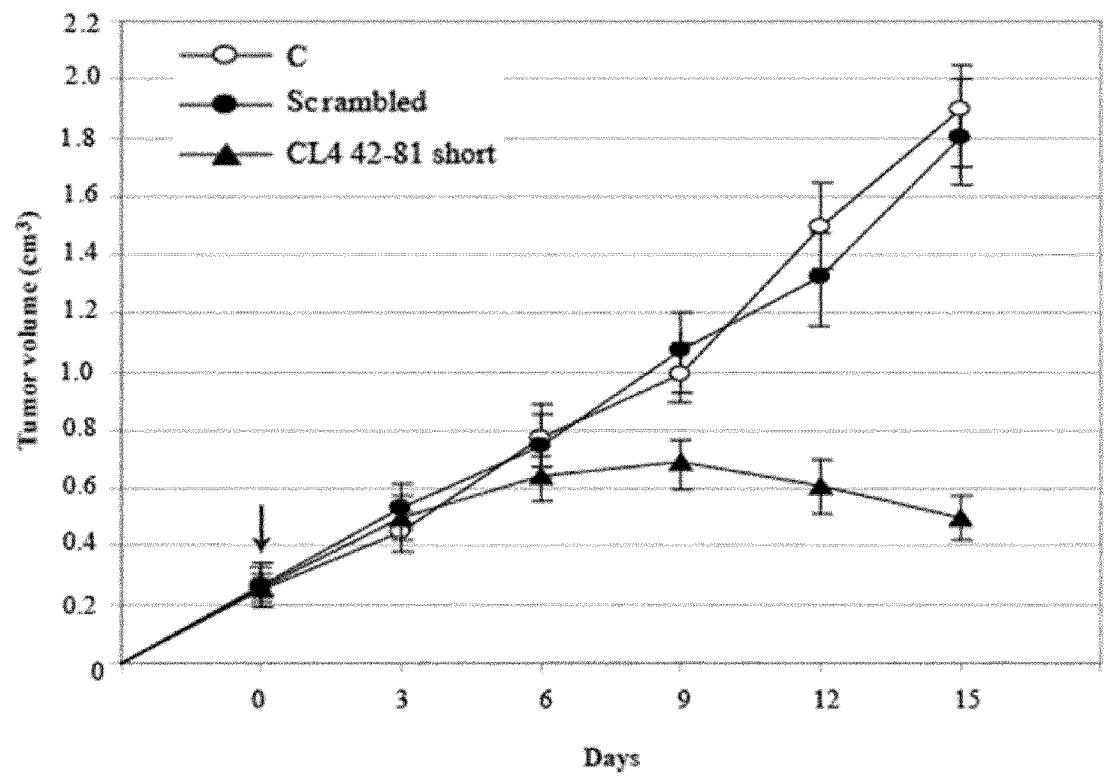
FIG. 7. CL4 42-81 aptamer inhibits tumor growth. CL4 42-81 aptamer or the scrambled aptamer were administered intratumorally in a mouse xenograft model bearing EGFR-overexpressing epidermoid carcinoma A431 cells. "C" is control, untreated mice group. The growth curves are plotted as the means tumor volume±s.e.m.

Tumors were then injected (Day 0) with 100 μl (200 pmoles) CL4 42-81 aptamer or the scrambled RNA used as negative control. The injections were administered three time a week for the following two weeks. Tumors were measured every 3 days. As shown in FIG. 7, a pronounced reduction in tumor volume was observed for A431 tumors treated with the CL4 42-81 aptamer. Indeed, from day 9 to day 15 the CL4 42-81-treated tumors stopped to grow and was reduced in volume. Suppression of tumor volume was specific to the CL4 42-81 treated group and was not observed with the control RNA.

The authors then assessed the efficiency of CL4 42-81 to inhibit A549 cell proliferation in vitro and limit tumor growth in vivo, in A549-mouse xenografts. As shown, treating A549 cells with CL4 42-81 for 24 and 48 h completely blocks [$^3$H]-thymidine incorporation (FIG. 8A). In addition, in A549-mouse xenografts a pronounced reduction in tumor volume was observed in the presence of CL4 42-81-treatment, leading at day 16 to 57% inhibition with respect to CL4 scrambled control (FIG. 8B) thus confirming the effect obtained in A431-mouse xenografts (FIG. 7). According with the effects observed in vitro, CL4 42-81-treatment of xenograft tumors decreases the extent of EGFR tyrosine phosphorylation and activates caspase-3 and -8 (FIG. 8C,D).

As a next step, the authors compared the inhibition effect on cell viability of the CL4 42-81 to that of two commercially available EGFR inhibitors that are currently in clinical use as anticancer therapeutics, gefitinib and cetuximab. In dose-dependent experiments (gefitinib, 0.1-10 µM and cetuximab, 0.05-1 µM), A549 cells resulted resistant at any concentration, even a high concentration of the above inhibitors. Interestingly, cells are highly sensitive to a 200 nM-final concentration CL4 42-81-treatment (FIG. 9A) and the same effect was observed on Calu1 and A431 (not shown). Further, as shown, the combined treatment of CL4 42-81 with cetuximab inhibited A549 cell viability more effectively than the treatment with each single agent alone, thus showing additive interactions. On the contrary, CL4 42-81 effectiveness was not improved when administered in combination with gefitinib. Most importantly, the synergy between CL4 42-81 and cetuximab was confirmed in vivo in mice xenografted with A549 cells (FIG. 9B,C). Indeed, the combination of CL4 42-81 and cetuximab decreased the number of proliferating Ki-67-positive cells and increased the number of apoptotic cells stained positively for terminal deoxynucleotidyl transferase mediated dUTP nick end labeling (TUNEL) more efficiently than the treatment of each inhibitor alone. Whether the aptamer and the antibody bind to different epitopes on the receptor, remain to be determined.

Discussion

Dysregulation of human ErbB/HER pathways by overexpression or constitutive activation can promote tumor processes including angiogenesis and metastasis and is associated with poor prognosis in many human malignancies. Accordingly, the ErbB receptor family with the most prominent members EGFR and ErbB2, represents validated targets for anti-cancer therapy.

In the present invention, the authors identified a nuclease resistant RNA-aptamer (named CL4 42-81) that specifically binds to the extracellular domain of the human EGFR.

The CL4 42-81 aptamer recognizes specifically the EGFR receptor expressed on the surface of EGFR-positive cells (NSCLC, breast, epidermoid carcinoma, glioma, NIH/EGFR) as well as the purified soluble extracellular domain of the receptor both in monomeric and dimeric form. On the other hand, it does not bind to the other ErbB family members: ErbB2, ErbB3 or ErbB4.

The treatment of tumour EGFR-positive cells with the aptamer strongly affects many of the intracellular pathways that are essential for cancer development and progression. The mechanism of action of CL4 42-81 as inhibitor of the EGFR has been deeply investigated: the binding of the aptamer to cell-surface exposed EGFR results in blocking of the receptor activation, both if induced by homodimerisation and heterodimerisation with ErbB2 or ErbB3, thus in turn hampering the EGFR-dependent downstream signalling pathways (the anti-apoptotic STAT3 pathway and ERK pathway involved in cell proliferation). The aptamer does not bind and, consequently, does not function in cells that do not express EGFR.

As a consequence of the EGFR inhibition, CL4 42-81 strongly induces selective cell death of EGFR-positive cells as confirmed by the reduction in cell viability and the increase in the apoptotic sub-G1 peak. Further, the CL4 42-81 aptamer is able to strongly inhibit in vivo tumor growth in athymic mice bearing tumours derived from EGFR-overexpressing human cancer cells.

The present invention offers persuasive evidence for the clinical development of the CL4 42-81 aptamer as an antitumoral agent in EGFR-positive human tumors. In particular, in EGFR-positive tumors that are resistant to currently used therapeutic agents such as cetuximab or gefitinib. Further the CL4 42-81 aptamer may be advantageously used in combination with cetuximab, creating a synergy between the two agents.

In conclusion, the identification of CL4 42-81 aptamer specifically targeting the EGFR receptor opens the ways to the development of innovative cancer diagnostic and therapeutic strategies.

BIBLIOGRAPHIC REFERENCES

Amann J, et al. (2005) Cancer Res 65: 226-235.
Cardó-Vilaa M, et al. (2010) PNAS 107: 5118-5123.
Cerchia L, de Franciscis V, Condorelli G. "Method for obtaining oligonucleotide aptamers and uses thereof". International patent application WO 2010/023327
Cerchia L, et al. (2002) FEBS Letters 538: 12-16.
Cerchia L, et al. (2009) PLoS One 4 (11): e7971.
Cerchia L, de Franciscis V (2010) Trends Biotechnol. 28(10): 517-525.
de La Motte Rouge T, et al. (2007) Cancer Res 67: 6253-6262.
Hynes N E, Lane H A (2005). Nat Rev Cancer. 5(5):341-354.
Kruser T J, Wheeler D L (2010). Experimental cell research 316: 1083-1100.
Li N, et al. (2010) Chem. Commun 46: 392-394.
Li S, et al. (2005) Cancer Cell 7:310-311.
Lurje G and Lenz H J (2009) Oncology 77:400-410.
Mitsudomi T, Yatabe Y (2010) FEBS J 277:301-308.
Schlessinger, J (2004) Science 306: 1506-1507.
Spicer J, Harper P (2005) Int J Clin Pract 59: 1055-1062.
Yarden Y (2001) Eur J Cancer 37:S3-8.

The invention claimed is:

1. A method for treating an EGFR induced disorder, comprising administering a pharmaceutical composition to a patient in need thereof, the pharmaceutical composition comprising a nucleotide aptamer, wherein the nucleotide aptamer consists of the sequence 5' GCCUUAGUAACGUGCUUUGAUGUCGAUUCGACAGGAGGC 3' (SEQ ID NO: 1), and wherein the EGFR induced disorder is a hyperproliferative disorder.

2. The method according to claim 1, wherein the nucleotide aptamer is nuclease-resistant.

3. The method according to claim 1, wherein the pyrimidines of the nucleotide aptamer are 2'-fluoropyrimidine.

4. The method according to claim 1, wherein the EGFR induced hyperproliferative disorder is selected from the group consisting of cancer and primary tumour metastasis.

5. The method according to claim 4 wherein the cancer or primary tumour metastasis is selected from the group consisting of: gastrointestinal cancer, prostate cancer, ovarian cancer, breast cancer, head and neck cancer, lung cancer, non-small cell lung cancer, cancer of the nervous system, kidney cancer, retina cancer, skin cancer, liver cancer, pancreatic cancer, genital-urinary cancer and bladder cancer.

6. The method according to claim 1 wherein the EGFR induced disorder is resistant to treatment with cetuximab and/or gefitinib.

7. The method of claim 1 wherein the pharmaceutical composition consists of the nucleotide aptamer consisting of SEQ ID NO: 1.

8. The method according to claim 1, wherein the pharmaceutical composition further comprises another therapeutic agent.

9. The method according to claim 8, wherein the other therapeutic agent is cetuximab.

10. A method for diagnosing an EGFR induced disorder in a patient, from whom a sample is obtained, comprising:
incubating the obtained sample with a nucleotide aptamer; and
measuring the binding of the nucleotide aptamer to the sample wherein the nucleotide aptamer consists of the sequence 5' GCCUUAGUAACGUGCUUUGAUGUCGAUUCGACAGGAGGC 3' (SEQ ID NO: 1), and wherein the EGFR induced disorder is a hyperproliferative disorder.

11. The method according to claim 10 wherein the sample is a blood, serum or saliva sample, a biopsy, urine or cerebrospinal fluid.

12. A kit for the diagnosis of an EGFR induced disorder in a patient from whom a sample is obtained, the kit comprising a nucleotide aptamer, wherein the nucleotide aptamer consists of the sequence 5' GCCUUAGUAACGUGCUUUGAUGUCGAUUCGACAGGAGGC 3' (SEQ ID NO: 1)), and wherein the EGFR induced disorder is a hyperproliferative disorder.

* * * * *